United States Patent [19]

Fernandez de Castro

[11] E Re. 31,517

[45] Reissued * Feb. 7, 1984

[54] METHOD FOR QUANTITATIVE DETERMINATION OF RENIN ACTIVITY IN BLOOD EMPLOYING PHENYL METHYL SULFONYL FLUORIDE AND POLYETHYLENE GLYCOL

[76] Inventor: Aurora L. Fernandez de Castro, 54657 David Dr., Elkhart, Ind. 46514

[ * ] Notice: The portion of the term of this patent subsequent to Nov. 11, 1992 has been disclaimed.

[21] Appl. No.: 943,251

[22] Filed: Sep. 15, 1978

Related U.S. Patent Documents

Reissue of:

[64] Patent No.: 3,984,532
Issued: Oct. 5, 1976
Appl. No.: 611,669
Filed: Sep. 9, 1975

U.S. Applications:

[63] Continuation-in-part of Ser. No. 419,623, Nov. 28, 1973, Pat. No. 3,919,407.

[51] Int. Cl.[3] ..... G01N 33/54; G01N 33/56; C12Q 1/34; C12Q 1/44

[52] U.S. Cl. ..... 436/539; 435/4; 435/7; 435/18; 435/19; 435/269; 435/272; 436/542; 436/811; 436/822; 436/824; 436/825; 436/826

[58] Field of Search ..... 424/1, 1.5, 12; 23/230 B; 435/7, 4, 18, 19, 269, 272; 436/542, 535, 811, 822, 824, 825, 826

[56] References Cited

U.S. PATENT DOCUMENTS 3,843,775 10/1974 Wolf ..... 424/1
3,899,298 8/1975 Szczesniak ..... 421/1

OTHER PUBLICATIONS

Fahrney, et al., JACS, vol. 85, pp. 997-1000, (1963).
Khairallah, et al., Biochem. Med., vol. 1, pp. 1-8, (1967).
Pickens, et al., Circ. Res., vol. 17, pp. 438-448, (1965).
Overturf, M. L., "Social Physiological & Biochemical Characteristics of a Hypertensive Population", Ph. D. Thesis, Univ. Iowa, (Aug. 1970).
Overturf, M., et al., J. Chron. Dis., vol. 25, pp. 621-624, (1972).
Fitz, et al., Abstract from Clin. Res., vol. 20, p. 312, (1972).
Boaz, et al., Abstract from Clin. Res., vol. 21, p. 801, (1973).
Katz, et al., Clin. Chem., vol. 18, No. 6, pp. 528-533, (1972).
Jambhi, et al., Abstract from Western Section, Clinical Research, vol. 14, p. 149, (1966).
Strong, et al., J. Lab. Clin. Med., vol. 79, No. 1, pp. 170-180, (1972).
Chem. Abstr., vol. 76, SS609e, (1972), Citing Nigawara et al., Nippon Hinyokika Sakkai Zasshi, vol. 62, No. 4, pp. 298-307, (1971).
Sealey, et al., Kidney International, vol. 1, pp. 240-253, (1972).
Sealey, et al., Am. J. Med., vol. 55, pp. 303-314, (1973).
Sealey, et al., Seminars in Nuclear Medicine, vol. 5, No. 2, pp. 189-202, (1975).
Kodish et al., J. Lab. Clin. Med., vol. 83, No. 5, pp. 705-715, (1974).
Goodfriend, T., "Radioimmunoassay of Angiotension and Measurement of Angiotension Activity", Distributed at V.A. Workshop on RIA in Hypertension, V.A. Hospital, Denver, Colo., Sep. 27-30, 1972.
"PRC Assay", Distributed at V.A. Workshop on RIA in Hypertension, V.A. Hospital, Denver, Colo., Sep. 27-30, 1972.
"Plasma Renin Activity by Radioimmunoassay of Angiotension I, Dist. at V.A. Workshop on RIA in Hypertension, V.A. Hospital, Denver, Colo., Sep. 27-30, 1972.
Katz, "Radioimmunoassay of the Renin System", Dist. at V.A. Workshop on RIA in Hypertension, V.A. Hospital, Denver, Colo., Sep. 27-30, (1972).
Barrett et al., Clin. Chem., vol. 18, No. 11, pp. 1339-1342, (1972).

*Primary Examiner*—Teddy S. Gron
*Attorney, Agent, or Firm*—A. A. Saffitz

[57] ABSTRACT

A method for the quantitative determination of renin activity in blood utilizing the measurement of Angiotensin I by treating the blood with ethylenediaminetetraacetic acid (EDTA) and the plasma with phenylmethyl sulfonylfluoride (PMSF) at a preferred pH to ascertain the full range of concentration where PMSF is effective for accurate and quick determination.

Also, a method for the quantitative determination of renin activity in blood utilizing the measurement of Angiotensin I by incubating the samples after antibody addition at room temperature (23° to 30° C.) for 1 to 2 hours and separating the free from the antibody bound species with polyethylene glycol after having treated the blood with ethylenediaminetetraacetic acid (EDTA) and the plasma with phenylmethyl sulfonylfluoride (PMSF) at a preferred pH. PMSF offering enough protection against Angiotensin I destruction at room temperature that in combination with polyethylene glycol at a preferred pH the time required for the radioimmunoassay determination is 1 to 2 hours at room temperature instead of 24±2 hours at 4° C. which takes with charcoal in the presence of other inhibitors and making the system less succeptible to time dependent errors.

2 Claims, No Drawings

METHOD FOR QUANTITATIVE DETERMINATION OF RENIN ACTIVITY IN BLOOD EMPLOYING PHENYL METHYL SULFONYL FLUORIDE AND POLYETHYLENE GLYCOL

Matter enclosed in heavy brackets [ ] appears in the original patent but forms no part of this reissue specification; matter printed in italics indicates the additions made by reissue.

CROSS-REFERENCE TO RELATED APPLICATIONS

This application is a Continuation-In-Part of my application entitled, Method and Reagent for Quantitative Determination of Renin Activity in Blood, Ser. No. 419,623, filed Nov. 28, 1973, now U.S. Pat. No. 3,919,407, issued Nov. 11, 1975.

BACKGROUND OF THE INVENTION

1. Field of the Invention

The measurement of plasma renin activity (PRA) is considered of primary importance in the investigation of hypertensive conditions. For example, it is widely employed to determine whether hypertension is due to primary aldosteronism or secondary aldosteronism. Both conditions reveal a high aldosterone secretion rate; primary aldosteronism occuring with a low renin activity, secondary aldosteronism exhibiting a high renin activity. It is, then, important to distinguish between low renin values and the lower part of the normal spectrum. In other words, conditions under which plasma renin activity are measured must be maximized to differentiate truly low renin values from the low but normal values. Most commercial kits on the market that determine Angiotensin I as a measure of PRA have neglected this consideration and, as a result, cannot differentiate between truly low renin values and low but normal values.

Plasma renin activity (PRA) is generally measured by the quantitative determination of Angiotensin I. Angiotensin I can be lost after it has been produced if it is not effectively inhibited as can be seen from the multireaction system shown below.

| | | |
|---|---|---|
| (1) Angiotensinogen | $\xrightarrow{\text{Renin}}$ | Angiotensin I |
| (2) Angiotensin I | $\xrightarrow[Ca^{++}, Mg^{++}]{\text{Converting enzyme}}$ | Angiotensin II + Dipeptide |
| (3) Angiotensin II | $\xrightarrow{\text{Angiotensinase}}$ | Inactive Peptides |

It is of fundamental importance then to have one or more compounds present in this system, which will serve as inhibitors of the side reactions and will therefore prevent the loss of Angiotensin I.

In addition, the measurement of Angiotensin I is now assuming importance in the study of platelet-dependent thrombotic phenomena. A stimulation of immunoreactive material resembling prostaglandin E by Angiotensin II has been reported. Prostaglandin secretion by endothelium appears to exercise a significant role in platelet-dependent thrombotic phenomena and in local control of vascular permeability as reported by Gimbrone and Alexander. Angiotensin II may be directly monitored by its precursors Angiotensin I. Obviously, an accurate and rapid method will meet a presently growing need for Angiotensin I monitoring in the clinical patient.

2. Description of the Prior Art

I have found in my application Ser. No. 419,628, filed Nov. 28, 1973, that using phenylmethyl sulfonylfluoride (PMSF) at a final concentration of 1.32 mg/ml plasma and adjusting the pH of the plasma to pH 6.0 the yield of Angiotensin I measured is optimized when compared with Hydroxyquinoline and Dimercaprol or with Diisopropylfluorophosphate (DFP) for which clinically normal values have been established. In this method the addition of PMSF was such as to make the sample dilution negligible.

In addition, commercially available kits for the measurement of plasma renin activity (PRA) by determination of Angiotensin I use an incubation period of 24±2 hours at 4° C., after the addition of antibody using charcoal to separate the free from the antibody bound specie in the radioimmunoassay. This long incubation at 4° C. makes it impossible to obtain results in the laboratory the same day that the sample arrives. Also, the use of charcoal to separate the free from the antibody bound specie requires the step of carefully removing each supernatant from the pellet after centrifugation as charcoal pellets are easily disturbed. Furthermore, as charcoal is a non-specific adsorbant, the time elapsed between the addition of charcoal and the centrifugation of the tubes is rather critical creating a real possible source of error, if many samples are being processed.

Reports have appeared in the literature, Clinical Chemistry, by M. James Barrett and Patricia S. Cohen, Vol. 18, pages 1339–1342, 1972, suggesting the use of polyethylene glycol in sodium barbital buffer (25 mmol/liter, pH 8.6) to separate free from antibody bound specie after incubation of 24±2 hours at 4° C. using inhibitors which do not yield optimal amounts of Angiotenin I. This technique also makes it impossible to assay the sample the same day that it is received in the laboratory.

The different methods can be summarized in the chart, which follows:

Present Method:

-continued

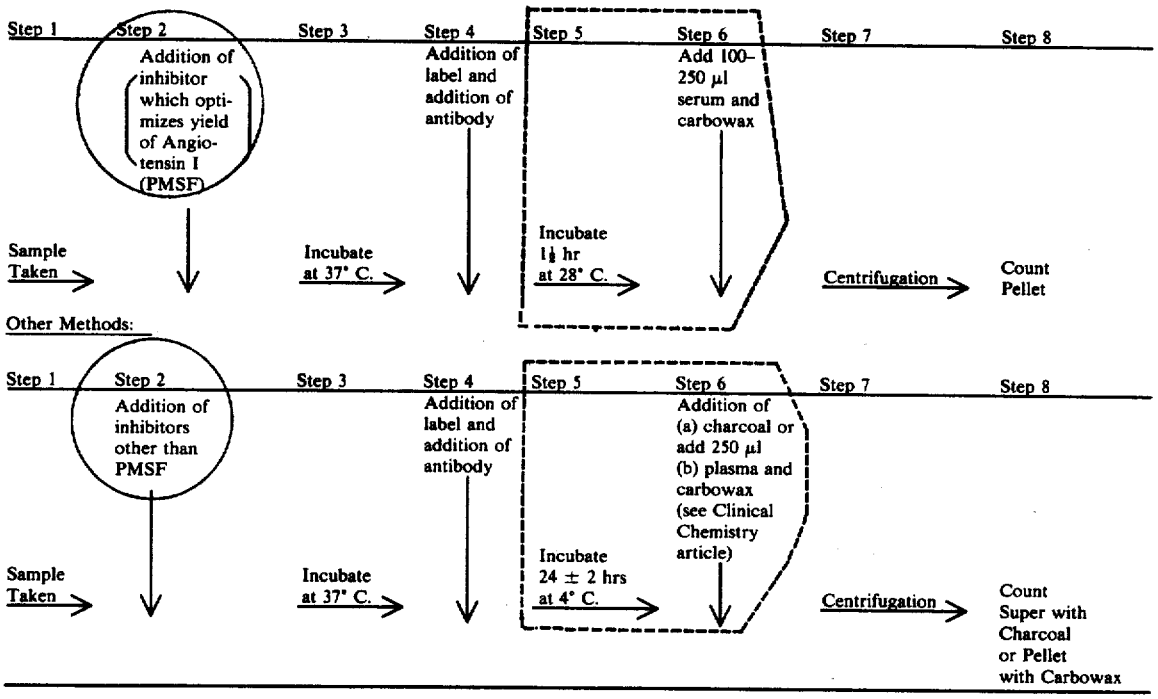

In the above chart, the steps within the dotted circles in the presence of PMSF as inhibitor provide the same quantitative results. These steps are after addition of label and antibody so that the method is specific as a part of the radioimmunoassay and in no other methodology.

The advantages are as follows:

1. time of second incubation is reduced from 24±2 hours to 1 to 2 hours, allowing the test to be done the same day;

2. time dependent errors are avoided with polyethylene glycol instead of charcoal, as charcoal is a nonspecific adsorbant the time element after addition of charcoal and before centrifugation (step 7) is critical. In other words, if one uses charcoal and doesn't centrifuge immediately, it starts adsorbing what it should not, see article in Clinical Chemistry by Barret and Cohen; and, 3. technician's time involved in the separation of the free from the bound specie after centrifugation is substantially shortened and errors are avoided in this separation step.

As the pellet formed after centrifugation when using polyethylene glycol is not easily disturbed, and it is this pellet in advantage 3, above, that one counts, all supernatants can be discarded in one operation by simply inverting the rack of tubes (when tubes are firmly held by the rack). The pellets remaining firmly attached to the bottom of the tubes. By contrast, the careful separation of the supernatant, which one counts in the case of charcoal, from the easily disturbed charcoal pellet (after centrifugation) requires much more careful handling of each individual tube and demands more of the technician's labor. This labor can be considerable if the number of samples being processed is large. In addition, a possible error in this step is introduced unless careful separation is achieved.

OBJECTS OF THE INVENTION

It is the object of the present invention to ascertain the full range of concentrations where the inhibitor PMSF is effective for accurate determination and to ascertain the precise conditions for quick determination of Angiotensin I in plasma.

It is a further object of the present invention to provide a method, yielding the optimal amount of Angiotensin I in plasma, and simultaneously substantially reducing the time and minimizing the time dependent errors in the assay of Angiotensin I. This technique allows for optimal results to be obtained the same day that the sample is received in the laboratory.

BRIEF SUMMARY OF THE INVENTION

In accordance with the invention, PMSF exhibits its inhibitory effects against Angiotensin I destruction between 0.013 mg and 13.2 mg PMSF per ml of plasma. The effectiveness of its inhibitory capacity varying widely between these ranges and should be taken into consideration when accurate and quick determination of Angiotensin I is being made.

This aspect of the invention which relates to the broad concentration of effectiveness of PMSF finds use in both radioactive and non-radioactive testing.

Also, in accordance with the invention, the yield of Angiotensin I by radioimmunoassay is the same upon incubating the reaction mixture (after antibody addition) for 1 to 2 hours at 23° to 30° C. and subsequent addition of polyethylene glycol (12% to 18% final concentration) in 0.01 M Tris hydroxymethylaminomethane (Tris) buffer pH about 7.0 or distilled water pH 5.6 to 6.5 or when incubating the reaction mixture mixture (after antibody addition) for 24±2 hours at 4° C. and subsequent addition of charcoal, when PMSF (0.013 mg to 13.2 mg) is used as inhibitor at a specified pH. The optimal pH being about 6.0.

This aspect of the invention relating to polyethylene glycol is uniquely adapted for radioimmunoassay testing.

DETAILED DESCRIPTION OF THE INVENTION

The reagents used are:

1. Phenylmethyl sulfonylfluoride—(Sigma Chemical Co.) Solution of these reagents in ethanol were made and added to plasma as to give final concentrations between 0.013 mg and 13.2 mg PMSF per ml of plasma.
2. Dimercaprol solution—(E. R. Squibb & Sons, Inc.) 300 mg 2-3 dimercaptopropanol and 600 mg benzyl benzoate in 3 ml peanut oil.
3. 8-Hydroxyquinoline solution—(E. R. Squibb & Sons, Inc.) 660 mg dissolved in 10 ml of water.
4. Diisopropylfluorophosphate—(Sigma Chemical Co.) 0.1 ml Diisopropylfluorophosphate (DFP) in 1.9 ml isopropyl alcohol.
5. Polyethylene glycol solutions:
   a. 24% to 36% polyethylene glycol (carbowax 6000 flakes, Schwarz-Mann) solutions in 0.01 M Tris hydroxymethylaminomethane (Tris) buffer at pH 7.0. These solutions are referred to as 24% or 36% carbowax. As the carbowax solutions are added to 1 ml of solution, the final concentration of carbowax is 12% to 18%.
   b. Similar solutions of carbowax were made in distilled water. The pH of the water when tested with pH paper was between 5.6 and 6.5. These solutions were also added to 1 ml of solution.
6. $I^{125}$ Angiotensin I, Angiotensin I standard, Angiotensin I antibody, and charcoal were purchased as a kit (E. R. Squibb & Sons, Inc.). These reagents were prepared and used following the manufacturers directions.

DETAILED DESCRIPTION OF THE PREFERRED METHOD EMBODIMENT

The collection of blood should be in a cold Vacutainer containing EDTA (liquid EDTA preferred), inverted several times and packed in ice immediately. Centrifugation is carried out in the cold to collect the plasma. The plasma is kept in ice if processed within 2 hours or it can be frozen at −10° C. until ready for use. In preparing the sample, if the sample has been frozen, it is allowed to thaw while immersed in crushed ice. It should be noted that from the time the plasma sample is obtained, all manipulations are carried out in the cold (4° C.), unless otherwise specified.

Using a pH meter, the pH of the sample is adjusted to the desired pH with 0.5 M HCl while different volumes of phenylmethyl sulfonylfluoride (PMSF) solutions are added so that the final concentration is between 0.013 and 13.2 mg PMSF per ml of plasma. Other inhibitors are added to other samples for purpose of comparison. Either 10 μl of 8-Hydroxyquinoline solution and 10 μl of Dimercaprol solution per ml of plasma are added according to the manufacturer's directions or 20 μl of Diisopropylfluorophosphate per ml of plasma according to the published literature. The mixture is then vigorously mixed and divided into four aliquots. In the incubation, one of the four aliquots per specimen, two are placed in a shaking water bath at 37° C. for usually 3 hours. The other two aliquots, to be used as blanks, are kept in the ice bath (about 4° C.) for the same amount of time.

In the radioimmunoassay, to four tubes containing 1 ml of diluted $I^{125}$ Angiotensin I, 50 and 10 μl from each of the two aliquots incubated at 37° C. are added. These two sets of different size aliquots are considered duplicates. To two other tubes, 50 μl are added from each of the two aliquots incubated at 4° C. These two tubes represent duplicate blanks. To all the tubes, 50 μl of Angiotensin I antiserum are added. After Angiotensin I antiserum is added, one of the following procedures is followed:

a. The mixture is incubated at 4° C. for 24±2 hours. At the end of the incubation period 1.0 ml of charcoal suspension is added to all tubes. The mixture is then mixed gently and centrifuged for 5 minutes at 3,000 to 4,000 rmp. (During this separation step, the charcoal suspension should be added only to the quantity of tubes that can be centrifuged simultaneously as the equilibrium of the antigen-antibody reaction is altered upon prolonged contact with the charcoal—manufacturer's directions). The supernatant is carefully separated from the pellet and the radioactivity counted; or, b. The mixture is incubated for 1 to 2 hours at room temperature 23° to 30° C. The tubes are then placed at 4° C. Then, 100 μl (or up to 250 μl) of serum or any equivalent material containing similar quantities of immunoglobulins are added to aid in the precipitation of immunoglobulins in the plasma followed by 1 ml of carbowax solution (24% to 36% carbowax). The tubes are left at 4° C. for 10 minutes (or 30 minutes or up to 2 hours) then centrifuged at 5,000 rpm for 15 minutes. The supernatant is poured off, the tubes are allowed to drain for 2 minutes and the radioactivity of the pellet counted. The pouring off of the supernatant can be accomplished in one step by inverting the entire rack of tubes (when all the tubes are well fitted in the rack). The supernatant is discarded.

A standard curve is prepared by setting up tubes with known amounts of Angiotensin I and following the same procedure used with the samples.

Table I shows the results of Angiotensin I obtained when the plasma samples were adjusted to pH 6.0 and different concentrations of PMSF were added. The samples were incubated, after antibody additions, for 24 hours at 4° C. and charcoal was used to separate the free from the bound specie. The results obtained usng Dimercaprol and Hydroxyquinoline together or DFP instead of PMSF are also shown. These other inhibitors are shown as the clinically normal range for Angiotensin I has been established using these inhibitors.

Each number shown in Table I is the average or 6 determinations. The same is true for Table III (shown later).

Table I shows that, as shown in our previous patent, the addition of 1.32 mg PMSF per ml of plasma gives greater yield of Angiotensin I than using Hydroxyquinoline and Dimercaprol and as good a yield of Angiotensin I as when treating the sample with the very toxic DFP.

When the concentrations of PMSF are varied to 0.66 mg/ml plasma (0.5 times the original 1.32 mg/ml plasma), 0.132 mg/ml plasma (0.1 times the original 1.32 mg/ml plasma) and 0.013 mg/ml plasma (0.01 times the original 1.32 mg/ml plasma), the yield of Angiotensin I decreases by 10%, 26% and 65%, respectively, when compared with 1.32 mg PMSF/ml.

On the other hand, when the concentration of PMSF is increased to 6.60 mg/ml plasma (5 times the original 1.32 mg/ml plasma) and 13.2 mg/ml plasma (10 times the original 1.32 mg/ml plasma), there is first an increase of about 30%, then a decrease of about 74%, respectively.

Thus, if an error in addition of the inhibitor PMSF is made, one must be aware of the difference in yield of Angiotensin I when comparing the results obtained in a patient with the clinically normal values reported for Angiotensin I.

In addition, as when the concentration of PMSF is around 6.6 mg PMSF/ml of plasma shows a further yield of Angiotensin I, clinically normal values should be reestablished to maximize the yield.

The above percentages are representative of average values obtained in my studies, but I have found that the values can vary about 10% in different plasma samples from different individuals.

I have used 1.32 mg PMSF/ml plasma as my base line for comparison with other PMSF concentrations, as it gives about the same values as with DFP. The clinical normal values for DFP have been established and therefore each individual result obtained in the laboratory must be compared with these values in order to interpret the numbers obtained. The present method has proved its accuracy.

The above percentages, although obtained in a small sample population, give guidelines for making meaningful interpretations where comparing the results obtained in the laboratory with the clinically established range of results if an error of addition with the inhibitor PMSF occurred and is taken into account.

Thus, with the above explained procedure, and using the Tables herein, it is possible to perform meaningful analysis in a situation where a second sample of venous blood may not be possible to obtain under the precisely controlled conditions of blood drawing from the veins of the right and left kidneys in the clinical procedure for differential renal plasma renin activity, which is an essential part of the diagnosis for surgically correctable reno-vascular hypertension. It is now possible for the first time to achieve reliable clinical data even though errors have been detected in the procedure.

For example, if one gets an average of 8.6 ng Angiotension I/ml/hr in a plasma sample to which one has added (1.32×5) mg PMSF/ml of plasma (instead of 1.32) one should be aware that for that patient the value that one must compare with the clinically established range is 6.0±0.6 ng Antiotensin I/ml/hr and not 8.6 as the above difference of concentration of inhibitor PMSF gives an enhancement of 30% (±10%) in Angiotensin I. If, on the other hand, one adds by mistake (1.32×10) mg PMSF/ml of plasma (instead of 1.32) and gets 1.6 ng Angiotensin I/ml/hr, the value for that patient, which one should compare with the clinically established range, is still 6.0±0.6, and not 1.6 as this error in addition shows a decrease of 74% (±10%) in the Angiotensin I obtained, and so on.

Also, the higher values of Angiotensin I obtained in plasma treated with about 6.6 mg PMSF/ml of plasma may shed further light on the mechanism of inhibition of this compound.

When the samples are adjusted to pH 5.0 or 7.5, the same concentrations of PMSF appear similarly effective in the inhibition of Angiotensin I destruction although all results were lower than those obtained at pH 6.0, which is the optimal pH for Angiotensin I production.

Table II shows the results obtained when using carbowax or charcoal under different incubation conditions (24 hours at 4° C. with charcoal and 1½ hours at 28° C. with carbowax). The plasma samples were adjusted to pH 6.0 and 1.32 mg PMSF/ml or plasma were added to the plasma. As shown in this table, the results are very similar in either case.

Thus, by significantly decreasing the incubation time, optimal results can be obtained in the same day.

Similar results between the two incubation conditions are obtained when the samples are adjusted to pH 5.0 to 7.5 except that, all values are lower than those obtained at pH 6.0.

For latter reference, it should be pointed out here that in the experiments shown in Table II, the samples were allowed to stand at 4° C. after carbowax addition and before centrifugation, for 10 minutes.

Table III shows the amounts of Angiotensin I obtained when the concentration of PMSF is varied in plasma samples at pH 6.0 and carbowax is used in the shorter incubation method. Comparison with Table I shows that the range of concentration of PMSF in plasma, namely, 0.013 to 13.2 mg PMSF/ml of plasma, follows the same pattern of effectiveness as with the longer incubation method. As in the case of charcoal, similar but lower results are obtained at pH 5.0 or 7.5.

Table IV shows the results obtained when after addition of carbowax and before centrifugation, the samples are placed at 4° C. for 30 minutes. All other conditions are the same as those in Table II. Comparison of Tables II and IV show that the time elapsed between the addition of carbowax and centrifugation of the samples is not critical as identical results are obtained. The results do not vary even after 2 hours at 4° C. instead of 30 minutes.

The fact that the time elapsed is not critical (in contrast to the charcoal methodology) allows to centrifuge together a large number of samples after carbowax has been added without time dependent errors.

TABLE I

Plasma renin activity using different concentrations of PMSF at pH 6.0.

Incubation conditions: 24 hours, 4° C.

Method of separation: charcoal

| Inhibitor Used | Final Concentration of PMSF (mg/ml plasma) | PRA (ng Angio I/ml/hr) | % Difference[1] |
|---|---|---|---|
| Hydroxyquinoline and Dimercaprol[2] | | 1.5 | 35% |
| DFP[2] | | 2.3 | 0% |
| PMSF | 0.0132 (1.32 × 0.01) | 0.8 | 65% |
| PMSF | 0.132 (1.32 × 0.1) | 1.7 | 26% |
| PMSF | 0.66 (1.32 × 0.5) | 2.1 | 9% |
| PMSF | 1.32 | 2.3 | |
| PMSF | 6.60 (1.32 × 5) | 3.3 | 30% |
| PMSF | 13.2 (1.32 × 10) | 0.6 | 74% |

[1]% difference was obtained setting the highest of the two values being compared to 100%

[2]amounts used described under reagents

TABLE II

Plasma renin activity using carbowax or charcoal to separate free from bound species at different incubation conditions. Standing time at 4° C. after carbowax addition is 10 minutes.

| Sample No. | PRA ng Angiotensin I/ml/hr 15% Carbowax[1] (final concentration) Incubation: 1½ hr at 28° C. | Charcoal Incubation: 24 hr at 4° C. |
|---|---|---|
| 1 | 2.2 | 2.0 |
| 2 | 3.8 | 3.9 |
| 3 | 0.9 | 0.8 |
| 4 | 1.6 | 1.4 |
| 5 | 1.7 | 1.9 |
| 6 | 2.4 | 2.3 |
| 7 | 1.3 | 1.3 |
| 8 | 3.5 | 3.3 |

[1]200 μl of serum added before carbowax addition

TABLE III

Plasma renin activity using different concentrations of PMSF at pH 6.0.

Incubation conditions: 1½ hours, 28° C.

Method of separation: carbowax (15% final concentration)

| Inhibitor Used | Final Concentration of PMSF (mg/ml plasma) | PRA (ng Angio I/ml/hr) | % Difference[1] |
|---|---|---|---|
| Hydroxyquinoline[2] and Dimercaprol | | 1.5 | 37% |
| DFP[2] | | 2.3 | 4% |
| PMSF | 0.013 (1.32 × 0.01) | 0.8 | 67% |
| PMSF | 0.132 (1.32 × 0.1) | 1.7 | 29% |
| PMSF | 0.66 (1.32 × 0.5) | 2.2 | 8% |
| PMSF | 1.32 | 2.4 | |
| PMSF | 6.60 (1.32 × 5) | 3.4 | 29% |
| PMSF | 13.2 (1.32 × 10) | 0.6 | 75% |

[1]% difference obtained setting the highest of the two values being compared to 100%

[2]amounts used described under reagents

TABLE IV

Plasma renin activity using carbowax or charcoal to separate free from bound species at different incubation conditions. Standing time at 4° C. after carbowax addition is 30 minutes.

| Sample No. | PRA ng Angiotensin I/ml/hr 15% Carbowax[1] (final concentration) Incubation: 1½ hr at 28° C. | Charcoal Incubation: 24 hr at 4° C. |
|---|---|---|
| 1 | 2.1 | 2.1 |
| 2 | 3.7 | 3.8 |
| 3 | 0.9 | 0.8 |
| 4 | 1.4 | 1.3 |
| 5 | 1.9 | 1.7 |
| 6 | 2.5 | 2.5 |
| 7 | 1.4 | 1.2 |
| 8 | 3.4 | 3.2 |

[1]200 μl serum added before carbowax addition

In the foregoing examples, the temperature for incubation is illustrated at 28° C., but the incubation is equally effective at temperatures of about 23° C. to about 30° C. for a time period of about 1 hour to about 2 hours, although the preference is about 2 hours.

Also the amount of serum to aid in the precipitation of immunoglobulins in the plasma used before carbowax addition may vary from about 100 μl to about 250 μl, but preferably and for the technicians' convenience, smaller amounts should be used, e.g., about 100.

Although Tables II and IV are shown with 200 μl of serum added, the same results can be obtained with 100 μl.

Further, the carbowax concentration shown in Tables II and IV is about 15% final concentration, but equally good results are obtained if the carbowax is 12% to 18% (final concentration).

Also, interestingly, if the carbowax solutions were made in distilled water rather than Tris buffer, similar standard curves and results were obtained.

This shows that neither the particular ionic strength nor exact pH of the buffer is needed for the effectiveness of polyethylene glycol in separating the free from the bound species, and that as long as polyethylene glycol is present within the specified final concentration range, the buffer is not necessary.

In summary, the methodology presented here gives a faster and more error free method for the determination of Angiotensin I in serum. In addition, as the data in Tables I and III give representative percentages obtained in our sample population, these percentages provide useful guidelines in obtaining meaningful answers for patients' results where errors in the addition of inhibitor are made.

The use of Tris buffer pH 7.0 was made originally as proteins are known to denature in either very acid or very basic pH, therefore, our selection of a neutral pH.

The fact that distilled water (pH 5.6–6.5) gave similar results as the above mentioned buffer was an interesting and significant finding.

What is claimed is:

1. In a method for measuring plasma renin activity in a sample of plasma comprising adding ethylene diamine tetraacetic acid, adding inhibitor to inhibit Angiotensin I destruction, incubating at about 37° C. to release Angiotensin I from the plasma sample, adding $I^{125}$ labeled Angiotensin I while adding antibody, incubating the labeled mixture sample and antibody and adding a material to separate free Angiotensin I from Angiotensin I bound to antibody prior to determining the amount of Angiotensin I that improvement consisting of:

adding phenyl methyl sulfonyl fluoride as the inhibitor;

adjusting the pH from 5 to 7.5 after adding the inhibitor;

incubating the labeled mixture of sample and antibody for 1 to 2 hours at about 23° C. to 30° C. after the incubation at 37° C. to yield Angiotensin I for measurement;

separating the free Angiotensin I from the Angiotensin I bound to antibody with polyethylene glycol in 0.01 Molar Tris hydroxymethyl aminomethane at pH 7 in a concentration of 12% to 18% based on the total medium, in the presence of about 100 μl to 250 μl of serum or any equivalent material containing similar quantities of immunoglobulins to aid precipitation of immunoglobulins in the plasma; and, said incubating and separating steps being carried out one after the other, allowing for the optimal yield of Angiotensin I to be obtained in the same day that the sample is received and minimizing time dependent errors occurring therein.

2. A method of measuring plasma renin activity in a plasma sample comprising adjusting the plasma pH from 5 to 7.5 in the presence of ethylenediaminetetraacetic acid and in the presence of between 0.013 and 13.2 mg phenylmethyl sulfonylfluoride per ml of plasma as inhibitor against Angiotensin I destruction, incubating at about 37° C. to release Angiotensin I from the plasma, adding $I^{125}$ labeled Angiotensin I while adding antibody to Angiotensin I, thereafter, incubating to allow reaction with antibody to Angiotensin I and adding a substance to separate the free Angiotensin I from the Angiotensin I bound to antibody prior to determining the amount of Angiotensin I, that improvement consisting of incubating for 1 to 2 hours at about 23° C. to 30° C. and separating free from bound Angiotensin I, using polyethylene glycol at a 12% to 18% final concentration in a pH range provided by 0.01 M tris hydroxymethylaminomethane at pH 7.0 or by distilled water at pH 5.6 to 6.5 in the presence of about 100 μl to 250 μl of serum or any equivalent material containing similar quantities of immunoglobulins and said incubating and separating steps being carried out one after the other allowing for the optimal yield of Angiotensin I to be obtained in the same day that the sample is received and minimizing time dependent errors occurring in the separation as compared to separations using solid adsorbent materials.

[3. In a method for measuring plasma renin activity in a sample of plasma comprising adding ethylenediaminetetraacetic acid while adjusting the pH of said sample, adding inhibitor to prevent Angiotensin I destruction, incubating at about 37° C. to release Angiotensin I from the sample and thereafter determining the amount of Angiotensin I thus released that improvement consisting of adding as the inhibitor phenylmethyl sulfonylfluoride in a range of concentration between 0.013 mg/ml to 13.2 mg/ml of plasma sample while simultaneously adjusting the pH to 5 to 7.5.]

* * * * *